United States Patent [19]

Bewert et al.

[11] 4,226,799

[45] Oct. 7, 1980

[54] α-AMINOMETHYLENE-β-FORMYLAMINO-PROPIONITRILE AND ITS MANUFACTURE

[75] Inventors: Wolfgang Bewert, Frankenthal; Wolfgang Littmann, Mannheim, both of Fed. Rep. of Germany

[73] Assignee: BASF Aktiengesellschaft, Fed. Rep. of Germany

[21] Appl. No.: 951,567

[22] Filed: Oct. 16, 1978

[30] Foreign Application Priority Data

Oct. 27, 1977 [DE] Fed. Rep. of Germany ....... 2748153
Apr. 26, 1978 [DE] Fed. Rep. of Germany ....... 2818156

[51] Int. Cl.³ .......................................... C07C 87/452
[52] U.S. Cl. ................. 260/465 E; 544/163; 544/329; 546/246; 260/465 D; 260/465 R
[58] Field of Search .......... 260/465 D, 465 E, 465 R; 544/163; 546/246

[56] References Cited

U.S. PATENT DOCUMENTS

| 3,901,888 | 8/1975 | Leimgruber et al. ............ 260/465 R |
| 3,954,756 | 5/1976 | Maruyama et al. .................. 544/329 |
| 4,032,559 | 6/1979 | McCall et al. .................... 260/465 R |

*Primary Examiner*—Donald G. Daus
*Assistant Examiner*—James H. Turnipseed
*Attorney, Agent, or Firm*—Keil & Witherspoon

[57] ABSTRACT

An improved method of manufacture of 2-methyl-4-amino-5-formylaminomethylpyrimidine (II), wherein a N-substituted or unsubstituted α-aminomethylene-β-formylaminopropionitrile (I) is reacted with acetamidine.

Compound II is an intermediate for the manufacture of vitamin $B_1$.

6 Claims, No Drawings

α-AMINOMETHYLENE-β-FORMYLAMINOPROPIONITRILE AND ITS MANUFACTURE

The present invention relates to N-substituted and unsubstituted α-aminomethylene-β-formylaminopropionitrile, which is used to manufacture 2-methyl-4-amino-5-formylaminomethylpyrimidine (II) and to its manufacture from metal salts of α-formyl-β-formylaminopropionitrile (III). Compound II is an important intermediate for the manufacture of vitamin $B_1$.

German Laid-Open Application DOS No. 2,323,845 discloses that compound II may be manufactured by methylating compound III with dimethyl sulfate and reacting the resulting enolether with an amidine.

We have found that 2-methyl-4-amino-5-formylaminomethylpyrimidine of the formula II

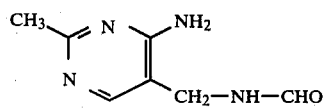

may be manufactured in a simple manner, avoiding the use of the toxic product dimethyl sulfate, by a method wherein a salt of α-formyl-β-formylaminopropionitrile (III)

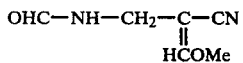

where Me is a cation, preferably an alkali metal cation or alkaline earth metal cation, is reacted with a salt of ammonia or of an amine, of the formula

where the radicals R are hydrogen or identical or different alkyl, aryl or aralkyl or, together with the nitrogen, form a heterocyclic ring, to give the novel α-aminomethylene-β-formylaminopropionitrile of the formula I

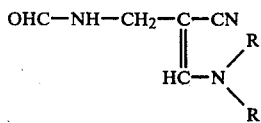

where R has the above meaning, and this compound is cyclized with acetamidine to give the pyrimidine II.

Regarding the manufacture of the starting compound III, reference may be made to German Laid-Open Application DOS No. 2,323,845. The compound is obtained, for example, by reacting β-aminopropionitrile with an ester of formic acid or carbon monoxide in the presence of a metal alcoholate.

The metal salts, especially the alkali metal salts, of α-formyl-β-formylaminopropionitrile may be used for the reaction with the salt of ammonia or of the amine

either after they have been isolated or in the form of the reaction mixture obtained from the process of manufacture starting from β-aminopropionitrile.

Suitable compounds

are ammonia and primary or secondary, open-chain or cyclic amines. Specific examples are ammonia, monomethylamine, monoethylamine, dimethylamine, diethylamine, n-propylamine, iso-propylamine, dibutylamine, morpholine, piperidine, N-methylaniline and especially aniline. Any other primary or secondary amine may also be used, but it is advantageous to employ those of 1 to 20, preferably of 1 to 10, carbon atoms.

The amines are advantageously used in the form of their salts, preferably the salts of hydrogen halides, in particular in the form of their hydrochlorides.

As a rule, the ammonium salt is reacted in stoichiometric amount, or near-stoichiometric amount, with the metal salt of the compound III.

The reaction is advantageously carried out at an elevated temperature; preferably the mixture is heated to the boiling point of the solvent used, until about 1 mole of water has been eliminated.

Examples of suitable solvents are alcohols, eg. methanol, hydrocarbons, eg. benzene, and chlorohydrocarbons, eg. chloroform. Accordingly, the temperatures used are, for example, up to about 100° C. Under these conditions the reaction is complete within a short time, for example from 15 to 120 minutes. The enamine I is obtained by filtering the hot solution and concentrating the filtrate.

In a preferred embodiment of the invention, the amine hydrochloride is reacted with the metal salt of α-formyl-β-formylaminopropionitrile in aqueous solution, the resulting enamine being extracted with a water-immiscible solvent which is inert under the reaction conditions.

Specifically, an advantageous procedure is to prepare an aqueous solution of the amine hydrochloride and to stir the salt of α-formyl-β-formylaminopropionitrile into this solution. A clear solution results, from which the product is extracted continuously.

The reaction takes places so smoothly that the extraction can be started immediately after addition of the propionitrile. The concentration of the aqueous solution is not critical but it is advisable only to employ such amounts of water that complete solution of the salt is only just ensured.

The reaction proceeds even at room temperature. In general, temperatures of from 20° to 100° C. can be employed. Temperatures outside this range may also be employed but offer no advantage.

Examples of solvents which may be employed for the extraction include polar and non-polar solvents, eg. esters, aromatic hydrocarbons and chlorohydrocarbons. Specific examples are ethyl acetate, methylene chloride and toluene.

Mere evaporation of the extractant gives the enamine I in good purity; this product can be reacted directly with acetamidine to give the pyrimidine derivative.

The reaction with acetamidine in an alcohol, eg. ethanol or methanol, to give the pyrimidine II, is carried out by the method described in German Laid-Open Application DOS No. 2,323,845 for the starting material α-alkoxymethylene-β-formylaminopropionitrile.

The resulting pyrimidine II is formed in good yield and may be used directly for the manufacture of vitamin $B_1$.

EXAMPLE 1

82.2 parts by weight of 90 percent pure sodium salt of α-formyl-β-formylaminopropionitrile are suspended in 550 parts by volume of benzene and the suspension is refluxed with 71.2 parts of aniline hydrochloride for 1 hour; the reaction mixture is then filtered hot and the filtrate is concentrated to half its volume. After isolating the product, and concentrating the mother liquor further, a total of 85.3 parts of α-anilinomethylene-β-formylaminopropionitrile of melting point 119° C., corresponding to 84.9% of theory, based on the Na salt, is obtained.

EXAMPLE 2

74 parts of 75 percent pure sodium salt of α-formyl-β-formylaminopropionitrile are refluxed for 1 hour with 58.3 parts of aniline hydrochloride in 400 parts by volume of methanol, the reaction mixture is filtered, and the filtrate is concentrated to half its volume. 59.6 parts of α-anilinomethylene-β-formylaminopropionitrile are obtained, followed by a further 6.3 parts after concentrating the mother liquor; this corresponds in total to 87.4% of theory, based on the Na salt.

EXAMPLE 3

98.6 parts of 75 percent pure sodium salt of α-formyl-β-formylaminopropionitrile and 81.5 parts of dimethylammonium chloride in 700 parts by volume of chloroform are refluxed for 1.5 hours, during which time 8.5 parts (theory: 9 parts) of water are eliminated. The mixture is filtered, the filtrate is concentrated to dryness and the product is recrystallized from methanol. 43.0 parts of α-dimethylaminomethylene-β-formylaminopropionitrile of melting point 90° C. are obtained.

The following are obtained in the same way:

| Example | Amine | Method of Example | Melting point | Yield, % of theory |
|---------|-------|-------------------|---------------|--------------------|
| 4 | morpholine . HCl | 3 | oil | 56% |
| 5 | diethylamine . HCl | 1 | 56–58° C. | 56.7% |
| 6 | n-propylamine . HCl | 1 | oil | 41.3% |
| 7 | di-n-butylamine . HCl | 1 | oil | 92% |
| 8 | N-methylaniline . HCl | 1 | 80–82° C. | 54.6% |

EXAMPLE 9

94 parts of aniline are emulsified in 500 parts of water and 230 parts by volume of concentrated hydrochloric acid are run in so as to form the hydrochloride. 150 parts of 80 percent pure sodium salt of α-formyl-β-formylaminopropionitrile are then stirred in at 80° C. and the solution is extracted continuously with ethyl acetate. After concentrating the ethyl acetate phase, 139 parts of enamine, ie. 86% of theory, are obtained analytically pure.

EXAMPLE 10

10.3 parts by weight of sodium methylate are added to a solution of 18 parts of acetamidine hydrochloride in 75 parts by volume of absolute ethanol, the mixture is stirred for 30 minutes at room temperature, undissolved constituents are filtered off, and 20.1 parts of α-anilinomethylene-β-formylaminopropionitrile, prepared as in Example 2, are added. The mixture is stirred for 20 minutes at 25°–30° C. and the resulting solution is concentrated to dryness. The product obtained is washed with 15 parts by volume of methanol and the methanol is removed. After repeating this purification operation and drying the product, 11.1 parts (calculated, 100% pure) of 2-methyl-4-amino-5-formylaminomethylpyrimidine are obtained.

We claim:

1. A compound of the formula $$\begin{array}{c} OHC-NH-CH_2-C-CN \\ \parallel \\ HC-N \diagdown R \\ \phantom{HC-N}\diagup R \end{array} \qquad I$$

where the R groups, which may be the same or different, represent hydrogen, alkyl, aryl or aralkyl or together with the nitrogen form a morpholine or piperidine ring, the total number of carbon atoms of the two R groups being 1 to 20.

2. The compound of the formula $$OHC-NH-CH_2-C(=CN)-HC-NH-C_6H_5$$

3. A process for the manufacture of a compound as claimed in claim 1, wherein an alkali metal or alkaline earth metal salt of α-formyl-β-formylaminopropionitrile is reacted with a salt of ammonia or of an amine of the formula $$HN{\diagdown R \atop \diagup R},$$

where the R groups are as defined in claim 1.

4. A process as claimed in claim 3, wherein α-formyl-β-formylpropionitrile is reacted with a salt of ammonia or of an amine of the formula $$HN{\diagdown R \atop \diagup R},$$

where the radicals R are as defined in claim 1, in aqueous solution and the resulting enamine of the formula I is extracted with a water-immiscible solvent which is inert under the reaction conditions.

5. A compound as defined in claim 1 wherein the total number of carbon atoms of the two R groups is from 1 to 10.

6. The compound of claim 1 wherein each R group is methyl.

* * * * *